United States Patent [19]

Bakker et al.

[11] 4,226,797

[45] Oct. 7, 1980

[54] PREPARATION OF MONOALKYL SULFURIC ACIDS AND THEIR SALTS

[75] Inventors: Pieter M. Bakker; Cornelis E. Kind; Volker G. Aurich, all of Amsterdam, Netherlands

[73] Assignee: Shell Oil Company, Houston, Tex.

[21] Appl. No.: 939

[22] Filed: Jan. 4, 1979

Related U.S. Application Data

[63] Continuation-in-part of Ser. No. 856,141, Nov. 28, 1977, abandoned.

[30] Foreign Application Priority Data

Nov. 30, 1976 [GB] United Kingdom ............... 49832/76

[51] Int. Cl.$^3$ ........................................... C07C 139/08
[52] U.S. Cl. .................................................... 260/460
[58] Field of Search ........................................ 260/460

[56] References Cited

U.S. PATENT DOCUMENTS

| 2,049,055 | 7/1936 | Fulton et al. | 260/460 |
| 2,640,070 | 5/1953 | Dahmen | 260/460 |

OTHER PUBLICATIONS

Gilbert, Sulfonation & Related Reactions, Interscience Publishers, N. Y., p. 343 (1965).

*Primary Examiner*—Natalie Trousof
*Assistant Examiner*—G. T. Breitenstein

[57] ABSTRACT

Secondary monoalkyl sulfuric acids are obtained in high selectivity and at a fast reaction rate in a process wherein $C_8$ to $C_{22}$ olefins are sulfated with sulfuric acid in the presence of a large amount of added secondary $C_8$ to $C_{22}$ alcohols. Additionally, the resulting sulphation reaction effluent containing secondary monoalkyl sulfuric acids may be neutralized to prepare the salts thereof, in which case the alcohols in the neutralization reaction product are recovered and recycled to the sulfation reaction zone.

23 Claims, No Drawings

PREPARATION OF MONOALKYL SULFURIC ACIDS AND THEIR SALTS

This application is a continuation-in-part of copending application Ser. No. 856,141, filed Nov. 28, 1977, now abandoned.

BACKGROUND OF THE INVENTION

The present invention relates to the production of secondary monoalkyl sulfuric acids and their salts. Such substances are widely known and have a broad range of recognized utility. For instance, the acids have been employed both as intermediates and as catalysts in organic synthesis and further as solvents in various formulations. The salts, particularly the sodium salts of secondary $C_8$ to $C_{22}$ monoalkyl sulfuric acids, are well known compounds with established utility as detergent components.

It is known to prepare monoalkyl sulphuric acids by reacting one or more $C_8$ to $C_{22}$ olefins, which may be internal or alpha-olefins, with sulfuric acid, said acid having a concentration of 75 to 100 percent by weight (%w). To prepare the corresponding salts the acids thus produced are neutralized with suitable bases, such as amines, or such as ammonium, alkali metal, or alkaline earth metal hydroxides, carbonates, or bicarbonates.

These two main reactions, i.e. sulphation and neutralization, may be illustrated by the following equations representing the preparation of secondary sulphate sodium salts from $C_8$ to $C_{22}$ alpha-olefins:

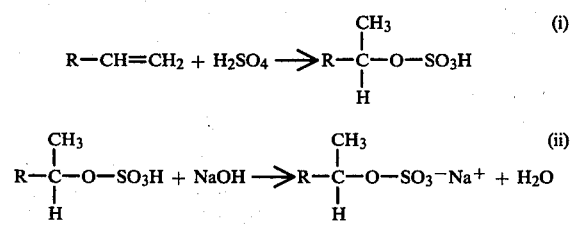

wherein R is an alkyl group of from 6 to 20 carbon atoms.

It is further known (U.S. Pat. No. 2,623,894; U.S. Pat. No. 2,640,070; British Pat. No. 691,929) that certain oxygen-containing compounds, present in the feed to the sulphation reaction in amounts up to 10%w, based on the weight of olefins in this feed, have a beneficial effect on the reaction rate or yield of monoalkyl sulphuric acids. Such oxygen-containing compounds include aliphatic alcohols, aldehydes, ketones, ethers, ether alcohols, carboxylic acids, sulphurous esters, and alkylphenol/alkylene oxide adducts. However, the production of monoalkyl sulphuric acids and their salts through these conventional processes is characterized by the formation of large quantities of secondary dialkyl sulphates (DAS) in the sulphation reaction. Although DAS formation may be suppressed by the presence in the sulphation reaction of the oxygen-containing compounds listed above, the quantity of DAS formed is still by no means fully acceptable. For example, when the sulphation reaction is carried out in the presence of aliphatic alcohols in amounts of up to 10%w, based on the weight of olefin, DAS is formed in amounts usually exceeding 40 mole percent (% mole), based on the monoalkyl sulphuric acid produced. DAS may be formed according to the following equations:

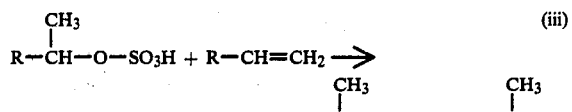

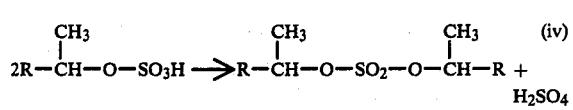

When it is desired to produce the monoalkyl sulfuric acid salts (MAS) from the acids, this problem of DAS formation is partly overcome by hydrolysis or saponification of the DAS to the desired MAS, suitably during the subsequent neutralization reaction, according to the equation:

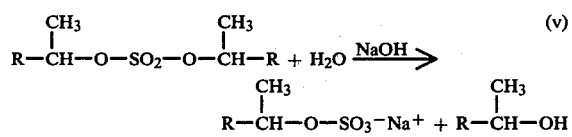

However, it can be seen that this is still only a partial solution to the problem since the hydrolysis also produces one mole of secondary alcohol which represents a loss of olefin. A further disadvantage of this known process for salt manufacture is that an amount of secondary alcohol is formed which is in excess of that which can be explained as a result of DAS hydrolysis. It is considered that this excess amount results from the hydration of olefins to alcohols during the sulphation reaction. The alcohols may, according to British Pat. No. 691,929, be recovered following neutralization of the monoalkyl sulfuric acids and used in the sulphation reaction, but while the amount thereof in the feed to the sulphation reaction is maintained below 10%w, on olefin, there will always ultimately be an excess of alcohol which has to be disposed of. One method of disposal (British Pat. No. 656,064) involves dehydration of the recovered alcohols to form olefins and the subsequent use of these olefins in further sulphation reactions. However, this method necessitates a separate dehydration reactor.

Thus, it would be highly desirable to reduce or eliminate by-product DAS and alcohol formation during the production of monoalkyl sulphuric acids and their salts.

SUMMARY OF THE INVENTION

It has now been found that secondary $C_8$ to $C_{22}$ monoalkyl sulphuric acids are obtained in high selectivity at a very fast reaction rate in a process which comprises sulphating an olefin reactant containing one or more $C_8$ to $C_{22}$ olefins by reacting said olefin reactant with sulphuric acid in the presence of at least 15% mole of one or more added $C_8$ to $C_{22}$ secondary alcohols, based on the moles of said olefin reactant. When olefin sulfation is carried out in this manner, the formation of dialkyl sulfate by-product is substantially reduced over that encountered in conventional practice utilizing lesser quantities of alcohol addition.

As an additional feature of the invention, it has been found that secondary $C_8$ to $C_{22}$ monoalkyl sulfuric acid salts are advantageously obtained in a process which comprises:

(a) sulphating, in a sulphation reaction zone, an olefin reactant comprising one or more $C_8$ to $C_{22}$ olefins by reacting said olefin reactant with sulphuric acid in the presence of at least 15% mole of one or more added $C_8$ to $C_{22}$ secondary alcohols, based on the moles of said olefin reactant, (b) neutralizing the secondary monoalkyl sulphuric acids so formed to yield the salts thereof, (c) recovering the $C_8$ to $C_{22}$ alcohols from the neutralization reaction product, and (d) recycling the recovered alcohols to the sulphation reaction zone.

By applying the critical amount of secondary alcohol recycle recited above, the production of salts according to this multi-step process of the instant invention can be carried out under conditions such that the quantity of alcohol recovered from the salts after the neutralization reaction is always substantially equal to the amount of alcohol added to the sulphation reaction zone, in which case the production of the monoalkyl sulphuric acid salts proceeds without the net production of alcohol and associated loss of olefin that is encountered in conventional processes.

DESCRIPTION OF THE PREFERRED EMBODIMENTS

According to the present invention, a process for preparing secondary monoalkyl sulphuric acids comprises sulphating, one or more $C_8$ to $C_{22}$ olefins with sulphuric acid in the presence of at least 15% mole, on olefin, of one or more added secondary $C_8$ to $C_{22}$ alcohols. Additionally, preparation of the salts of these acids can be advantageously accomplished by carrying out olefin sulfation in this manner and then subsequently neutralizing the acids so formed with a base to prepare the salts thereof, recovering one or more $C_8$ to $C_{22}$ alcohols from the neutralization reaction product, and recycling the recovered alcohol to the sulphation reaction zone.

The $C_8$ to $C_{22}$ olefins which may be used in the preparation of secondary monoalkyl sulfuric acids and their salts according to the present invention may be internal or alpha-olefins and may be linear or branched. Single cut olefins or mixtures of olefins may be used. $C_{12}$ to $C_{18}$ olefins are preferred, primarily because the salts produced from these olefins display better utility in detergent compositions.

The reaction conditions used in the sulphation reaction may vary between wide limits. Suitable reaction temperatures are from $-20°$ C. to $50°$ C., preferably from $0°$ C. to $40°$ C., and suitable residence times are from a few minutes to several hours, e.g. from 2 minutes to 10 hours, preferably from 5 minutes to 2 hours.

Usually a stoichiometric excess of sulphuric acid is used in the sulphation reaction over that required to sulphate the olefin(s). Suitable amounts are from 1.5 to 15 moles of sulphuric acid per mole of olefin plus alcohol.

The sulphuric acid used in the sulphation reaction may be of any suitable concentration, e.g. from 75 to 100%w in water. In fact, a further advantage of the present invention is that the reaction may be carried out with sulphuric acid of fairly low concentration, e.g. of from 75 to 90%w, preferably from 78 to 88%w. This is advantageous since it facilitates the removal of unconverted sulphuric acid. A principal means of removing the unconverted sulphuric acid from the sulphation reaction product is known as deacidification. Prior art processes, in which sulfuric acid of greater than 90%w concentration has generally been used, have called for de-acidification to be carried out by adding water, in one or more stages, to the sulphation reaction product to form separable sulphuric acid phase(s). However, addition of water also creates favorable conditions for the decomposition of alkyl sulphuric acids and necessitates the removal of large amounts of water from the separated sulphuric acid phase before the sulphuric acid can be re-used in the sulphation reaction. These problems may be overcome by using, in the sulphation reaction, sulphuric acid of a lower concentration, e.g. of below 90%w, since this concentration results in a separable sulphuric acid phase, containing most of the sulphuric acid, without the addition of water. After separation of this phase, any sulphuric acid which is still present in the remaining alkyl sulphuric acid phase may then be extracted by the addition of small amounts of water thereto. Thus since this preferred means of de-acidification is restricted to the use of sulphuric acid or less than 90%w concentration, it is advantageous that the process of the present invention may be carried out using sulphuric acid of from 75 to 90%w concentration. Both the first separated and the second separated sulphuric acid phases, the latter after concentration if necessary, may be re-used in the sulphation reaction. However, the present invention may be operated with sulphuric acid of higher concentration and/or without a de-acidification step.

Suitably, the secondary $C_8$ to $C_{22}$ alcohols used in the present invention have the same carbon chain length as, or a carbon chain length not differing by more than one, two or three carbon atoms from the carbon chain length of the olefin(s) to be sulphated since this gives the advantage that any sulphation of the alcohol that takes place will produce acids of substantially the same carbon chain length as those produced from the olefins. In other words, if one or more secondary $C_m$ alcohols are used in the present invention for accomplishing the sulphation of a $C_n$ olefin, where n and m represent integers between 8 and 22 inclusive, the alcohols may have the same carbon chain length (i.e., $m=n$), or a carbon chain length not differing by more than one (i.e., $n-1 \leq m \leq n+1$) two (i.e., $n-2 \leq m \leq n+1$), or three (i.e., $n-3 \leq m \leq n+3$) from the carbon chain length of the $C_n$ olefin. In fact, the alcohols to be used in the process of the invention may be derived by sulphating and hydrating the same olefin(s) that is to be used in the process.

The optimal amount of alcohol added to the sulphation reaction zone depends upon various factors such as the desired conversion of olefin and the chain length of the olefin being sulphated. In general, it has been found that the higher the conversion of olefin the higher is the amount of alcohol which should be added to the sulphation reaction zone. For example, if the olefin conversion is from 50 to 90% mole then the preferred amount of alcohol is from 40 to 150%, or more preferably from 45 to 100% mole, on olefin. However, if the desired olefin conversion is from 35 to 50% more then the preferred amount of alcohol may be below 40% mole, on olefin.

According to the invention, the presence of such alcohols in the feed to the reaction zone, wherein $C_8$ to $C_{22}$ olefins are sulphated with sulphuric acid to produce monoalkyl sulphuric acid, substantially reduces by-product formation. The use in this reaction feedstock of at least 15% mole, preferably at least 20% mole and most preferably at least 25% mole, of alcohol, on olefin, considerably reduces DAS formation, usually to below 25% mole, on monoalkyl sulphuric acid formed, while also considerably increasing the reaction rate. There appears to be no advantage, insofar as reducing DAS formation or increasing reaction rate is concerned, in increasing the alcohol concentration beyond 400% mole, on olefin.

The olefin sulphation reaction process of the invention finds particularly suitable application in a multi-step process for the production of monoalkyl sulphuric acid salts from olefins. In this aspect of the invention, the sulphation of the olefins to monoalkyl sulphuric acids is followed by neutralization to the corresponding salts, recovery of the alcohols from the neutralization reaction product, and recycle of the recovered alcohols to the sulphation reaction. By sulphation the olefin in the presence of at least 15% mole, on olefin of alcohol, it is possible to recover from the neutralization reaction product a substantially equal amount of the alcohol while achieving an acceptable conversion of olefin, i.e., above 30% mole. Thus, the process for the manufacture of monoalkyl sulphuric acid salts is preferably carried out in such a way that the alcohol balance, which is here defined as the molar ratio of the secondary $C_8$ to $C_{22}$ alcohol recovered from the neutralization reaction product to the secondary $C_8$ to $C_{22}$ alcohol added to the sulphation reaction zone, is substantially 1 (one). In practice an alcohol balance of from 0.75 to 1.25 may be acceptable. The finding that, by sulphating the olefin in the presence of at least 15% mole of alcohol, on olefin, it is possible to achieve an alcohol balance of substantially 1 (one) while achieving a satisfactory conversion of olefin to the salts, is considered very advantageous over prior art processes since it obviates the problems of continual net production and disposal of unwanted alcohol. Moreover, it is not necessary in the production of the salts to add, to the sulphation reaction zone, alcohol additional to that recovered from the neutralization reaction product, which means that it is not necessary to continually prepare additional alcohol for use in practicing this aspect of the present invention.

A further advantage for the production of monoalkyl sulphuric acid salts according to the present invention is that it is possible to start-up the process without any of the alcohol being added to the sulphation reaction, or by adding a secondary $C_8$ to $C_{22}$ alcohol in an amount of below 15% mole, on olefin, or by adding any amount of an alcohol other than a secondary $C_8$ to $C_{22}$ alcohol, e.g. one or more primary alcohols, to the sulphation reaction. Such flexibility in the start-up conditions is possible because the process is self-regulating, i.e. by recycling substantially the whole amount of recovered alcohols a situation is eventually reached in which the amount of recoverable alcohol will always be in excess of 15% mole, on olefin, at acceptable olefin conversions.

It is considered surprising that the process of the invention relating to production of monoalkyl sulphuric acids, by using amounts of alcohol within the aforesaid preferred range, may be operated so as to eliminate the net production of unwanted alcohol that characterized prior art processes. Without being bound by any particular theory, it is considered that this feature of the invention results from any production of alcohol by olefin hydration and DAS hydrolysis being compensated for by an equivalent loss of alcohol by sulphation.

According to this variation of the invention, the secondary monoalkyl sulphuric acids produced in the sulphation reaction are neutralized, optionally after de-acidification of the sulphation reaction product, to form the corresponding salts. Suitably such acids are neutralized by addition of aqueous solutions of bases such as amines or such as ammonium or alkali metal or alkaline earth metal hydroxides, carbonates or bicarbonates. Sodium hydroxide is the preferred base. The amount of base added clearly depends on whether or not the sulphation reaction product has been de-acidified. The base is suitably added as a 0.5 to 50%w aqueous solution in an amount ranging from 5 to 100%w of the olefin fed to the sulphation reaction. The neutralization of the acids is suitably carried out under conditions such that DAS present is hydrolyzed. Typically, a neutralization reaction temperature of from 50° to 100° C. and a neutralization reaction time of from 0.5 to 2.0 hours are used. It is possible to neutralize the acids at a lower temperature in which case it is desirable to heat the neutralization product to a higher temperature in order to hydrolyze any DAS present while adding sufficient base to neutralize the acids formed by such hydrolysis. After the neutralization reaction, the product may be de-salted. It may be desirable to use a de-salting treatment in place of or in addition to the de-acidification treatment described above depending on the extent of the de-acidification. Desalting is usually carried out by using an excess of base in the neutralization reaction which neutralizes the unconverted sulphuric acid to form the inorganic salts thereof in addition to neutralizing the alkyl sulphuric acids. These inorganic salts may be removed as a separate phase by the addition to the neutralization reaction product of various water soluble solvents such as lower alcohols and ketones. However, the removal of unconverted sulphuric acid in this way results in a loss of sulphuric acid, since the inorganic salts thereof are usually discarded. For this reason removal by de-acidification is preferred. Usually it is preferred that less than 20%w of inorganic sulphates, on monoalkyl sulphuric acid salts, are present in the final product.

In a further aspect of the process for the salt manufacture according to the present invention, the alcohol is recovered following the neutralization reaction and recycled to the sulphation reaction zone. Preferably, the process is operated in a continuous manner, such that the recovered alcohol is continuously recycled to the sulphation reaction zone. However, the process may be operated in a batch manner, in which case the removal alcohol is stored before it is recycled to the subsequent sulphation reaction step. In either case, the sulphation reaction zone may comprise two or more sulphation reactors.

The alcohol may be recovered from the neutralization reaction product by distillation but is preferably recovered by extraction using solvents such as an isopropyl alcohol (IPA)/gasoline mixture or certain ketones or acetates. (See the commonly assigned copending application, Ser. No. 856,811, filed Nov. 30, 1977, now abandoned) The extract thus obtained may be separated into a solvent fraction and an alcohol fraction by distillation. The alcohol fraction will also contain other non-surface active matter, such as olefins which have not been sulphated, and the whole of the unconverted organic matter may be recycled to the sulphation reaction zone.

The product obtained after extraction is an aqueous solution of the monoalkyl sulphuric acid salts containing various amounts of the solvent used in the extraction step. This product may be used as such as a detergent. However, the remaining amount of solvent together with some water may be removed, e.g., by distillation or partial evaporation to form a final product comprising an aqueous solution containing from 30 to 60%w MAS. As stated above, it is preferred that the final product comprise no more than 20%w of inorganic sulphates based on MAS.

To illustrate the manner in which the invention may be carried out, the following examples are given. It is to be understood that the examples are for the purpose of illustration only, and that the invention is not to be regarded as limited to any of the specific conditions cited therein.

EXAMPLES 1 to 9

Various mixtures of n-tetradecene-1 and secondary tetradecanol or secondary pentadecanol (prepared by sulphation and hydrolysis of n-tetradecene-1 or n-pentadecene-1, respectively) were sulphated. The amounts of alcohol used and the reaction times are given in Table I. In all cases the reaction was continued until an olefin conversion of 80% mole to the monalkyl sulphuric acid was obtained.

The reaction conditions used were:
 ratio of $H_2SO_4$ to olefin plus alcohol of 4 moles to one mole $H_2SO_4$ concentration of 84%w temperature of 10° C.

A part of the sulphation reaction product was removed for analysis of the monoalkyl sulphuric acid and dialkyl sulphate contents thereof.

The remaining sulphation reaction product mixture was then further processed according to the invention for the preparation of monoalkyl sulphuric acid salts. The sulphation product was first de-acidified by settling and then drawing-off the lower phase containing the sulphuric acid. The product was then further de-acidified through addition of 1.8 mole of water per mole of residual sulphuric acid followed by separation of the sulphuric acid phase which formed.

The de-acidified product was neutralized by reaction with NaOH (20%w in water) at 80° C. for 1 hour. The neutralization reaction product was then subjected to liquid/liquid extraction with a solvent mixture of IPA and gasoline containing 5%w of IPA.

The extract obtained, containing secondary alcohols, unreacted n-tetradecenes and various polymers, was distilled to remove the solvents therefrom and the amount and type of secondary alcohol was then determined. The amount of secondary alcohols formed per mole of secondary alcohol converted to sulphate (in the case of secondary pentadecanol) and the amount of secondary alcohol recovered per mole of secondary alcohol in feed were calculated and the results are given in Table I. The secondary alcohol together with unreacted n-tetradecenes and polymers was recycled to the sulphation reaction zone. The raffinate obtained was partially evaporated to remove the residual solvent and some water therefrom, producing an aqueous solution containing 40%w of the sodium salt of secondary monoalkyl sulphuric acid.

TABLE I

| Example | Amount of alcohol in feed (% mole on olefin) | Monoalkyl sulphuric acid preparation | | Monoalkyl sulphuric acid salt preparation | |
|---|---|---|---|---|---|
| | | Sulphation Reaction time (2) (min) | Dialkyl sulphate formed (% mole on monoalkyl sulphuric acid) | Amount of secondary alcohols formed (mole per mole of secondary/ (mole per mole alcohol converted to salt) (3) | Amount of secondary alcohol recovered of secondary alcohol feed) (4) |
| c (1) | 11.1 | 180 | 33 | 3.2 | 1.35 |
| 1 | 25 | 72 | 23 | 2.4 | 1.23 |
| 2 | 33.3 | 50 | 19.1 | 1.8 | 1.16 |
| 3 | 48 | 36 | 14.0 | 1.28 | 1.08 |
| 4 | 54 | 33 | 12.1 | 1.18 | 1.06 |
| 5 | 60 | 30 | 10.5 | 1.0 | 1.03 |
| 6 | 66.6 | 28 | 9.2 | 0.9 | 0.98 |
| 7 | 74 | 26 | 8 | 0.8 | 0.98 |
| 8 | 82 | 25 | 7 | 0.7 | 0.97 |
| 9 | 100 | 24 | 5.5 | 0.6 | 0.93 |
| 10 | 300 | 45 | 2.0 | 0.1 | 0.80 |
| 11 | 400 | 54 | 1.5 | 0.04 | 0.78 |

(1) = comparative (i.e. less than 15% mole alcohol on olefin)
(2) = time required to obtain 80% mole conversion of olefin
(3) = obtained by GLC calibrated with hexadecanol-2
(4) = obtained by GLC calibrated with starting alcohol

EXAMPLES 12 and 13

The procedure of Examples 1 to 11 was repeated using a mixture of n-tetradecene-1 and secondary pentadecanol comprising 100% of the alcohol, on olefin. The sulphation reaction conditions were the same except that $H_2SO_4$ of 79.6%w (Example 12) or 84.8%w (Example 13) was used. The results are given in Table II.

EXAMPLE 14

The procedure of Examples 1 to 11 was repeated using a mixture of internal tetradecenes and secondary pentadecanols (derived by sulphating and hydrolysing internal pentadecenes) comprising 100% mole of the alcohol on olefin. The reaction conditions were the same except that $H_2SO_4$ of 84.8%w was used. The results are given in Table II.

EXAMPLE 15

The procedure of Examples 1 to 11 was repeated using a mixture of n-tetradecene-1 and secondary pentadecanol comprising 100% mole of alcohol on olefin. The reaction conditions were the same except that in the sulphation reaction the $H_2SO_4$ to olefin plus alcohol molar ratio was 8 to one. The results are given in Table II.

TABLE II

| Example | Sulphation Reaction time (1) (min) | Dialkyl sulphate formed in the sulphation reaction (% mole on monoalkyl sulphuric acid) | Amount of Secondary alcohols recovered from the neutralization reaction (mole per mole of secondary alcohol in feed (2) |
|---|---|---|---|
| 12 | 450 | 4 | 0.79 |
| 13 | 6 | 7 | 0.93 |
| 14 | 90 | 6 | 0.78 |
| 15 | 10 | 3 | 0.97 |

(1) = time required to obtain 80% mole conversion of olefin.
(2) = obtained by GLC calibrated with starting alcohol.

EXAMPLE 16

A mixture of n-hexadecene and n-octadecene (1:1) was sulphated, neutralized and the reaction products extracted in an integrated continuous process using the reaction conditions of Examples 1 to 11 with the difference that the residence time in the sulphation reaction zone was 30 minutes. After steady-state conditions were achieved, the extract, after removal of the solvents therefrom, was continuously recycled to the sulphation reaction zone. After a further 1.5 hours of operation, the amount of recycled alcohols (secondary $C_{16}/C_{18}$ alcohols) remained substantially constant (26% mole on olefin feed). The amount of dialkyl sulphate formed in the sulphation reaction zone was 10% mole on monoalkyl sulphuric acid. The conversion of olefin to monoalkyl sulphuric acid salts in this example of the process was 47% mole. What is claimed is:

1. A process for preparing the salts of secondary monoalkyl sulphuric acids which comprises:
    (a) sulphating, in a sulphation reaction zone, an olefin reactant comprising one or more $C_8$ to $C_{22}$ olefins by reacting at a temperature from $-20°$ C. to $50°$ C. said olefin reactant with sulphuric acid, having an initial concentration between 75 and 100% by weight, in the presence of between 25 and 400% mole of one or more added $C_8$ to $C_{22}$ secondary alcohols, based on the moles of said olefin reactant, the amount of sulphuric acid added to the sulphation reaction zone being in the ratio of from 1.5 to 15 moles of sulphuric acid per mole of olefin plus alcohol added to said reaction zone,
    (b) neutralizing the secondary monoalkyl sulphuric acids so formed to yield the salts thereof,
    (c) recovering the $C_8$ to $C_{22}$ alcohols from the neutralization reaction product, and
    (d) recycling the recovered alcohols to the sulphation reaction zone.

2. The process of claim 1, wherein the concentration of the sulphuric acid is from 75 to 90% w.

3. The process of claim 2, wherein the sulphation reaction temperature is from $0°$ C. to $40°$ C.

4. The process of claim 3 wherein the sulphation reaction time is from 2 minutes to 10 hours.

5. The process of claim 4, wherein the molar ratio of the secondary $C_8$ to $C_{22}$ alcohols recovered from the neutralization reaction product to the secondary $C_8$ to $C_{22}$ alcohols added to the sulphation reaction zone is from 0.75 to 1.25.

6. The process of claim 5, wherein unconverted sulphuric acid is removed from the sulphation reaction product by de-acidification.

7. The process of claim 6, wherein the neutralization reaction is carried out at a temperature between $50°$ and $100°$ C.

8. The process of claim 7, wherein the one or more secondary $C_8$ to $C_{22}$ alcohols are recovered from the neutralization reaction product by extraction.

9. A process for preparing secondary monoalkyl sulphuric acids which comprises sulphating, in a sulphation reaction zone, an olefin reactant comprising one or more $C_8$ to $C_{22}$ olefins by reacting at a temperature from $-20°$ C. to $50°$ C. said olefin reactant with sulphuric acid, having an initial concentration between 75 and 100% by weight, in the presence of between 25 and 400% mole of one or more added $C_8$ to $C_{22}$ secondary alcohols, based on the moles of said olefin reactant, the amount of sulphuric acid added to the sulphation reaction zone being in the ratio of from 1.5 to 15 moles of sulphuric acid per mole of olefin plus alcohol added to said reaction zone.

10. The process of claim 9, wherein the concentration of the sulphuric acid is from 75 to 90% w.

11. The process of claim 10, wherein the sulphation reaction temperature is from $0°$ C. to $40°$ C.

12. The process of claim 11, wherein the sulphation reaction time is from 2 minutes to 10 hours.

13. A process for preparing secondary monoalkyl sulphuric acids which comprises sulphating, in a sulphation reaction zone, an olefin reactant comprising at least one $C_n$ olefin, wherein n is an integer between 8 and 22 inclusive, by reacting at a temperature from $-20°$ C. to $50°$ C. said olefin reactant with sulphuric acid, having an initial concentration between 75 and 100% by weight, in the presence of at least 15% mole, based on the moles of said olefin reactant, of one or more added $C_m$ secondary alcohols, wherein m is an integer between 8 and 22 inclusive, under the provision that $n-2 \leq m \leq n+2$, the amount of sulphuric acid added to the sulphation reaction zone being in the ratio of from 1.5 to 15 moles of sulphuric acid per mole of olefin plus alcohol added to said reaction zone.

14. The process of claim 13, wherein m is defined such that $n-1 \leq m \leq n+1$.

15. The process of claim 14, wherein m is defined such that $n=m$.

16. A process for preparing secondary monoalkyl sulphuric acids which comprises sulphating, in a sulphation reaction zone, an olefin reactant comprising at least on $C_n$ olefin, wherein n is an integer between 12 and 18 inclusive, by reacting at a temperature from $-20°$ C. to $50°$ C. said olefin reactant with sulphuric acid, having an initial concentration between 75 and 100% by weight, in the presence of at least 15% mole, based on the moles of said olefin reactant, of one or more added $C_m$ secondary alcohols, where m is defined such that $n-3 \leq m \leq n+3$, the amount of sulphuric acid added to the sulphation reaction zone being in the ratio of from 1.5 to 15 moles of sulphuric acid per mole of olefin plus alcohol added to said reaction zone.

17. A process for preparing secondary monoalkyl sulphuric acids which comprises sulphating, in a sulphation reaction zone, an olefin reactant comprising at least one $C_n$ olefin, wherein n is an integer between 8 and 22 inclusive, by reacting at a temperature from $-20°$ C. to $50°$ C. said olefin reactant with sulfuric acid, having an initial concentration between 75 and 100% by weight, in the presence of at least 20% mole, based on the moles of said olefin reactant, of one or more added $C_m$ secondary alcohols, wherein m is an integer between 8 and 22 inclusive, under the provision that $n-3 \leq m \leq n+3$, the amount of sulphuric acid added to the sulphation reaction zone being in the ratio of from 1.5 to 15 moles of sulphuric acid per mole of olefin plus alcohol added to said reaction zone.

18. A process for the preparation of secondary monoalkyl sulphuric acids which comprises reacting, in a sulphation reaction zone, at a temperature from $-20°$ C. to 50° C. a $C_n$ olefin with sulphuric acid, having an initial concentration between 75 and 100% by weight, in the presence of at least 15% mole of added $C_n$ secondary alcohol, wherein n is an integer between 8 and 22 inclusive, the amount of sulphuric acid added to the sulphation reaction zone being in the ratio of from 1.5 to 15 moles of sulphuric acid per mole of olefin plus alcohol added to said reaction zone.

19. A process for the preparation of monoalkyl sulphuric acids which comprises sulphating, in a sulphation reaction zone, an olefin reactant mixture comprising one or more $C_8$ to $C_{22}$ olefins by reacting, at a temperature from $-20°$ C. to 50° C. said olefin reactant mixture with sulphuric acid, having an initial concentration between 75 and 100% by weight, in the presence of at least 15% mole, based on the moles of said olefin reactant mixture, of one or more added $C_8$ to $C_{22}$ secondary alcohols, which alcohols have been obtained from the same said olefin reactant mixture by sulphation and hydrolysis or hydration, the amount of sulphuric acid added to the sulphation reaction zone being in the ratio of from 1.5 to 15 moles of sulphuric acid per mole of olefin plus alcohol added to said reaction zone.

20. The process of claim 19, wherein the amount of sulphuric acid added to the sulphation reaction zone is in the ratio of from 1.5 to 15 moles of sulphuric acid per mole of olefin plus alcohol added to said reaction zone.

21. The process of claim 19, wherein the concentration of the sulphuric acid is from 75 to 90% w.

22. The process of claim 21, wherein the sulphation reaction temperature is from 0° C. to 40° C.

23. The process of claim 22, wherein the sulphation reaction time is from 2 minutes to 10 hours.

* * * * *